US00PP20522P2

(12) United States Plant Patent
Kristensen

(10) Patent No.: US PP20,522 P2
(45) Date of Patent: Dec. 1, 2009

(54) ***OSTEOSPERMUM* PLANT NAMED 'SAKOST3586'**

(50) Latin Name: *Osteospermum hybrida*
Varietal Denomination: SAKOST3586

(75) Inventor: Niels G. Kristensen, Marslev (DK)

(73) Assignee: Sakata Ornamentals Europe A/S, Marslev (DK)

( * ) Notice: Subject to any disclaimer, the term of this patent is extended or adjusted under 35 U.S.C. 154(b) by 0 days.

(21) Appl. No.: 12/228,385

(22) Filed: Aug. 12, 2008

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette H Para
(74) *Attorney, Agent, or Firm*—Jondle & Associates, P.C.

(57) ABSTRACT

A new *Osteospermum* plant particularly distinguished by having yellow-orange flowers with a purple base and streaks of purple from the base of the petal to the tip, medium-large flowers and compact growth habit, is disclosed.

1 Drawing Sheet

Genus and species: *Osteospermum hybrida.*
Variety denomination: 'SAKOST3586'.

BACKGROUND OF THE NEW PLANT

'SAKOST3586' originated from a hybridization of proprietary hybrid *Osteospermum* breeding lines '203149' and '203148' in Aabyhoej, Denmark. The proprietary female parent, '203149' (unpatented) has a light bronze-yellow flower color with a terracotta-brown color at the flower petal apices. The proprietary male parent, '203148' (unpatented) has a deep rose-pink flower color that darkens toward the flower petal apices.

In spring 2004, the two *Osteospermum* lines were crossed and seeds were obtained. The seeds were sown and 300 plants were grown in pots for evaluation. Out of 300 $F_1$ lines, plant number 29 was selected for flower color and size.

In spring 2005, plant number 29 was vegetatively propagated by cuttings and evaluated in an open field and a greenhouse in Denmark. Plant No. 29 was given the code number '205036' and the stability of the distinct characteristics of this variety was confirmed.

In spring 2006, plants '205036' were evaluated again in pots and in an open field. The selection was named 'SAKOST3586' and was found to reproduce true to type in successive generations of asexual propagation.

SUMMARY OF THE INVENTION

The following are the most outstanding and distinguishing characteristics of this new cultivar when grown under normal horticultural practices in Salinas, Calif.

1. Yellow-orange flowers with a purple base and streaks of purple from the base of the petal to the tip;
2. Medium-large flowers; and
3. Compact growth habit.

DESCRIPTION OF PHOTOGRAPHS

This new *Osteospermum* plant is illustrated by the accompanying photographs which show the plant's overall plant habit including form, foliage and flowers. The photographs are of a plant grown 4 months from transplant date and six months from stick date in six inch pots from rooted cuttings in Salinas, Calif. in the spring of 2008. The colors shown are as true as can be reasonably obtained by conventional photographic procedures.

Figure 1:
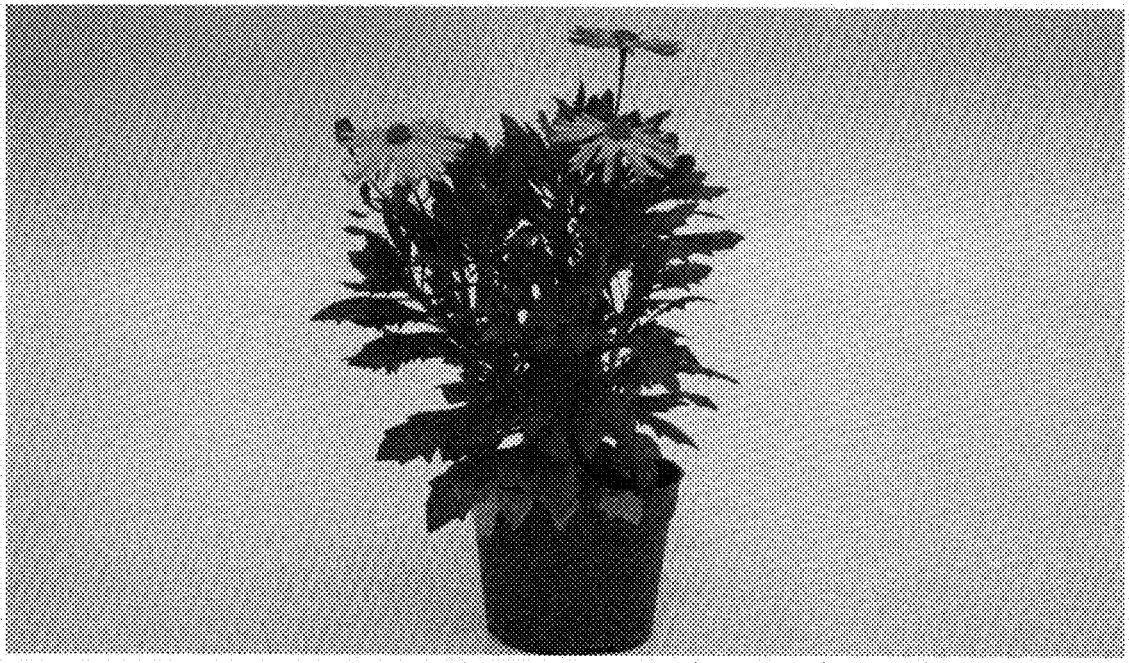
Figure 2:
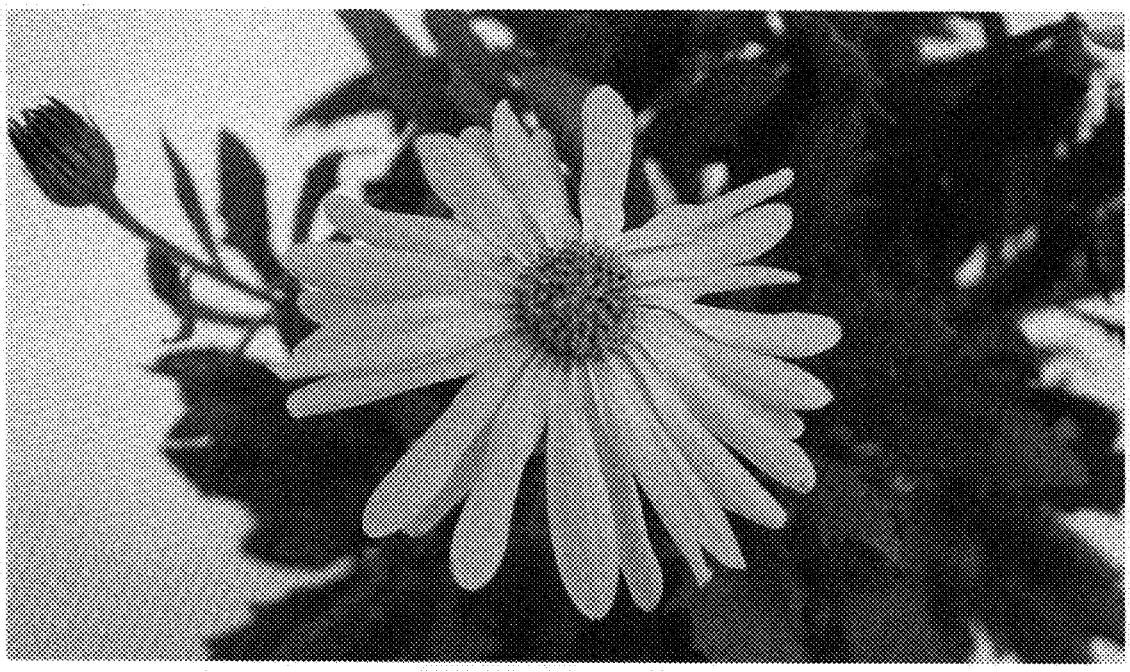

FIG. 1 shows overall plant habit of the plant grown in a pot.
FIG. 2 shows the mature inflorescence of the plant.

DESCRIPTION OF THE NEW CULTIVAR

The following detailed descriptions set forth the distinctive characteristics of 'SAKOST3586'. The data which define these characteristics were collected from asexual reproductions carried out in Salinas, Calif. Data was collected on plants grown approximately four months from transplant date and six months from stick date into 6-inch pots under greenhouse conditions in Salinas, Calif. in the spring of 2008. Color references are to the R.H.S. Colour Chart of The Royal Horticultural Society of London (R.H.S.), $4^{th}$ edition.

DESCRIPTION OF THE NEW PLANT

Classification:
*Family.*—Compositae.
*Botanical.*—*Osteospermum hybrida.*

Parentage:
*Female parent.*—A hybrid proprietary *Osteospermum* line '203149', having a light bronze-yellow flower color (unpatented).
*Male parent.*—A hybrid proprietary *Osteospermum* line '203148', having a deep rose flower color (unpatented).

Growth:
*Time to produce a rooted cutting.*—Cuttings will colonize a 2.5 cm. diameter by 2.5 cm. tall greenhouse tray cell with peat-based plant media in approximately four weeks. Cuttings are dipped in a normal dilution (1:9) of Dip 'N Grow root inducing solution in water. The trays are misted hourly during rooting.
*Environmental conditions for plant growth.*—Rooted cuttings are transplanted to pots with a 16 cm. diameter, one plant per pot. Peat-based growing media is used. The pots are watered using a 150–200 ppm fertilizer solution using 18-8-18 fertilizer. The soil is allowed to dry between watering. During the first few weeks after transplanting the plants should have evening temperatures around 15°–18° C. for good root growth. When plants reach 7.5–10 cm. in height they are pinched back to 5–6 leaves to promote branching. Spring and summer daytime high temperatures in Salinas, Calif., where the data was collected, range from 16°–25° C.

*Time to bloom from propagation.*—Approximately four weeks when rooted vegetative cuttings are transferred to a 5 inch diameter pot. Flowering season is all year in the United States. Vernalization is not required to induce flowering.

Plant description:

*Habit.*—Upright, tall.
*Life cycle.*—Perennial.
*Form.*—Erect, branching.
*Height (from soil line to first node).*—4.0 cm.
*Height (from soil line to top of foliage).*—30.0 cm.
*Width.*—32.0 cm.

Stems:

*General.*—Circular in cross section.
*Internode length.*—3.0 cm.
*Stem shape.*—Round.
*Stem diameter.*—0.4 cm.
*Stem color.*—RHS 143C (Green).
*Stem length (total).*—8.0 cm to 10.0 cm.
*Stem length (from soil to first node).*—4.0 cm.
*Stem length (between first and second nodes).*—3.0 cm.
*Pubescence.*—Very slight.
*Pubescence shape.*—Hair-like fibers, straight and short.
*Pubescence color.*—RHS N155A (White).
*Anthocyanin color.*—RHS N77C (Purple).

Leaves:

*Arrangement.*—Alternate.
*Shape.*—Oblanceolate.
*Apex.*—Acute.
*Base.*—Attenuate.
*Margin.*—Serrate.
*Venation.*—Anastomosing.
*Surface (both surfaces).*—Dull.
*Surface pubescence (both surfaces).*—Slight.
*Attachment.*—Decurrant.
*Length.*—7.0 cm.
*Width.*—3.0 cm to 3.5 cm.
*Thickness.*—Less than 0.1 cm.
*Color.*—Upper surface: RHS 139D (Green). Lower surface: RHS 138B (Green).
*Venation color (both surfaces).*—RHS 139D (Green).

Inflorescence:

*Number per plant.*—3.
*Type.*—Capitulum (head); disc florets are perfect and ray florets are carpellate.
*Flowering habit.*—Determinate.
*Lastingness of flowers.*—3 to 4 days.
*Fragrance.*—None.
*Seed production.*—None observed.
*Diameter.*—8.5 cm.
*Depth.*—1.5 cm.
*Petal number.*—33 per inflorescence.
*Disc diameter.*—3.0 cm.
*Disc floret number.*—80 to 100 per inflorescence.
*Peduncle length.*—8.0 cm from inflorescence to first node.
*Peduncle diameter.*—0.2 cm to 0.3 cm.
*Peduncle color.*—RHS 143C (Green).
*Peduncle texture.*—Dull, slight pubescence.
*Phyllaries.*—Arrangement: 24 per inflorescence, free, arranged symmetrically. Length: 1.5 cm. Width: 0.2 cm. Apex: Acute. Margin: Entire. Shape: Linear, acute. Color: Upper surface: RHS 138A (Green) with RHS 144D (Yellow-green) around the edge. Lower surface: RHS 138B (Green) with RHS 144D (Yellow-green) around the edge.

Ray florets (ligules):

*Corolla.*—One petal per ray floret; only the outer row of florets are the ray florets.
*Number of ray florets per inflorescence.*—33.
*Length.*—3.8 cm. to 3.9 cm.
*Width.*—1.0 cm.
*Shape.*—Lanceolate.
*Apex.*—Acute.
*Margin.*—Entire.
*Color.*—Upper surface: RHS 18A (Yellow-orange) at tip, RHS N78B (Purple) at the base with streaks of RHS N78C (Purple) from base to tip, with the color fading closer to the tip. Lower surface: RHS 12B (Yellow) with RHS N77D (Purple) streaks mostly at the center from base to tip; floret is RHS 155A (White) at base only.
*Pubescence.*—Glabrous.

Disc florets:

*Bud color.*—RHS 155A (White).
*Shape.*—Tubular.
*Apex.*—Rounded.
*Surface.*—Dull, pubescent.
*Size.*—Length: 0.1 cm. Width: 0.1 cm.

Reproductive organs:

*Ovary.*—Superior.
*Pistil form.*—One style with two stigma branches.
*Pistil length.*—0.2 cm.
*Stigma color.*—RHS N177A (Purple) around the edge of branches with RHS 155A (White) in the center.
*Style color.*—RHS 155A (White).
*Stamens.*—5, fused into a single tube.
*Anther color.*—RHS N77A (Purple).
*Pollen color.*—RHS 17A (Yellow-orange).
*Filament color.*—RHS 155A (White).

Disease and insect resistance: Very disease resistant, however, plants are susceptible to aphids, thrips, whiteflies and worms.

COMPARISON WITH PARENTAL LINES AND KNOWN CULTIVARS

'SAKOST3586' is a distinct variety of *Osteospermum* owing to its yellow-orange with streaks of purple flower color, medium-large flower size, flowers that stay open under low light conditions and compact growth habit. 'SAKOST3586' is distinguished from its parents primarily by its yellow-orange with streaks of purple flower color and medium-large flower size, as described in Table 1 (color references are to The Royal Horticultural Society Colour Chart, $4^{th}$ edition):

TABLE 1

Comparison with Parental Lines

| Characteristic | 'SAKOST3586' | '203148' | '203149' |
|---|---|---|---|
| Ray floret (ligule) color, upper surface: | Yellow-orange (RHS 18A) at tip and Purple (RHS N78B) at base with streaks of Purple (RHS N78C) from base to tip (fading out closer to tip) | Deep rose pink that darkens toward petal tip | Light bronze yellow with terracotta-brown at petal tip |
| Disc floret color | Yellow-grey/green | Grey-brown | Blue |
| Flower size | Medium-Large | Medium-Large | Large |

'SAKOST3586' is a distinct variety of *Osteospermum* owing to its unique terracotta color, medium-large flower size, flowers that stay open under low light conditions and compact plant growth habit. 'SAKOST3586' is most similar to the *Osteospermum* plant named 'Sideshow Copper Apricot' or 'Saksiscap' (Community Plant Variety Rights application granted Oct. 22, 2007, grant number CPVR No: 21062) and 'Saksiscopye' (U.S. plant Patent application Ser. No. 11/901,441); however, there are differences as described in Table 2 (color references are to The Royal Horticultural Society Colour Chart, $4^{th}$ edition):

TABLE 2

Comparison with Similar Variety

| Characteristic | 'SAKOST3586' | 'Saksiscap' | 'Saksiscopye' |
|---|---|---|---|
| Ray floret (ligule) color, upper surface: | Yellow-Orange (RHS 18A) at tip and Purple (RHS N78B) at base with streaks of Purple (RHS N78B) from base to tip (fading out closer to tip) | Copper with Purple at base | Yellow (RHS 12A) with slight streaks of Yellow-Orange (RHS 17A) and Greyed-Purple (RHS 187A) at tip |
| Ray floret (ligule) color, lower surface: | Yellow (RHS 12B) with Purple (N77D) streaks mostly at center from base to tip; floret is White (RHS 155A) at base only. | Copper-Brown | Greyed-purple (RHS 187A) with streaks of Yellow (RHS 12A) and Greyed-Purple (RHS 187A) at tip |
| Color of disc florets | Yellow-Grey/ Green | Pale Blue | Grey-Brown |
| Plant growth habit | Compact | Very compact | Very compact |
| Flower stalk length | Medium | Short | Short |

I claim:

1. A new and distinct cultivar of *Osteospermum* plant as shown and described herein.

* * * * *